(12) United States Patent
Mosier et al.

(10) Patent No.: US 8,790,904 B2
(45) Date of Patent: Jul. 29, 2014

(54) PROCESS FOR PREPARING ENRICHED GLUCAN BIOMASS MATERIALS

(75) Inventors: Nathan Mosier, West Lafayette, IN (US); Michael R. Ladisch, West Lafayette, IN (US); Brian Stater, Noblesville, IN (US); Bradley Spindler, Fishers, IN (US)

(73) Assignees: Purdue Research Foundation, West Lafayette, IN (US); Bowen Engineering Corporation, Indianapolis, IN (US)

( * ) Notice: Subject to any disclaimer, the term of this patent is extended or adjusted under 35 U.S.C. 154(b) by 0 days.

(21) Appl. No.: 13/446,542

(22) Filed: Apr. 13, 2012

(65) Prior Publication Data

US 2012/0322121 A1 Dec. 20, 2012

Related U.S. Application Data

(63) Continuation of application No. PCT/US2010/052495, filed on Oct. 13, 2010.

(60) Provisional application No. 61/251,034, filed on Oct. 13, 2009.

(51) Int. Cl.
*C12P 7/06* (2006.01)
*C12P 7/10* (2006.01)

(52) U.S. Cl.
USPC .......................................... 435/161; 435/165

(58) Field of Classification Search
USPC .................................................. 435/161, 165
See application file for complete search history.

(56) References Cited

U.S. PATENT DOCUMENTS

| 4,427,453 | A | * | 1/1984 | Reitter | 127/1 |
| 6,007,636 | A | | 12/1999 | Lightner | |
| 7,408,056 | B2 | | 8/2008 | Medoff et al. | |
| 7,585,652 | B2 | * | 9/2009 | Foody et al. | 435/163 |
| 2003/0154975 | A1 | | 8/2003 | Lightner | |
| 2004/0121436 | A1 | | 6/2004 | Blount | |
| 2011/0129889 | A1 | * | 6/2011 | Inamdar et al. | 435/165 |

OTHER PUBLICATIONS

Ohgren et al., Simultaneous saccharification and co-fermentation of glucose and xylose in steam-pretreated corn stover at high fiber content with *Saccharomyces cerevisiae* TMB3400. Journal of Biotechnology, vol. 126 (2006) pp. 488-498.*

Mosier et al., Characterization of dicarboxylic acids for cellulose hydrolysis. Biotechnology Progress, vol. 17 No. 3 (2001) pp. 474-480.*

(Continued)

*Primary Examiner* — Jon P Weber
*Assistant Examiner* — Kara Johnson
(74) *Attorney, Agent, or Firm* — Woodard, Emhardt, Moriarty, McNett & Henry LLP

(57) ABSTRACT

The disclosure describes a process for the conversion of lignocellulosic biomass to ethanol utilizing a dicarboxylic acid such as maleic acid as an enzyme mimic to hydrolyze the hemicellulose and cellulose of the biomass. Controlling the condition of the maleic acid hydrolysis can selectively hydrolyze the hemicellulose giving as a result a liquid portion rich in xylose and a solid portion rich in glucan. The glucan can be further hydrolyzed to produce a glucose containing material. The sugar materials can be fermented to produce ethanol which is recovered. The dicarboxylic acid is then recovered from the residue left after the ethanol is removed from the fermentation material, and the recovered dicarboxylic acid is recycled to the beginning of the process to treat additional lignocellulosic biomass.

20 Claims, 2 Drawing Sheets

(56) References Cited

OTHER PUBLICATIONS

Zhuang Xinshu, Study on Biomass Hydrolysis under Extremely Low Acids for Fuel Ethanol Production; Engineering Science and Technology I, 2006, No. 12, pp. 32-43; Dec. 31, 2006.

Jeffries, Thomas W. Comparison alternatives for the fermentation of pentoses to ethanol by yeasts. In: Lowenstein, Michael Z., ed. Energy applications of biomass: Proceedings of the National Meeting on Biomass R & D for Energy Applications; Oct. 1-3, 1984; Arlington, VA. New York, NY: Elsevier Applied Science Publishers; 1985: 231-252.

* cited by examiner

PROCESS FOR PREPARING ENRICHED GLUCAN BIOMASS MATERIALS

REFERENCE TO RELATED APPLICATION

This application is a continuation of International Application No. PCT/2010/052495, filed Oct. 13, 2010, which claims the benefit of U.S. Provisional Application No. 61/251,034, filed Oct. 13, 2009, now abandoned, each of which is hereby incorporated by reference in its entirety.

BACKGROUND

Increasing emphasis has been placed in recent years upon finding ways to efficiently produce fuels from renewable, non-petroleum resources. In one field of interest, fuel ethanol has been produced by fermentation of biomass feedstocks derived from plants. Currently, fuel ethanol is commercially produced from feedstocks of cornstarch, sugar cane and sugar beets. These materials, however, find significant competing uses in the food industry, and their expanded use to make fuel ethanol is met with increased prices and disruption of other industries. Alternative fermentation feedstocks and viable technologies for their utilization are thus highly sought after.

Lignocellulosic biomass feedstocks are available in large quantities and are relatively inexpensive. Such feedstocks are available in the form of agricultural wastes such as corn stover, corn fiber, wheat straw, barley straw, oat straw, oat hulls, canola straw, soybean stover, grasses such as switch grass, miscanthus, cord grass, and reed canary grass, forestry wastes such as aspen wood and sawdust, and sugar processing residues such as bagasse and beet pulp. Cellulose from these feedstocks is converted to sugars, which are then fermented to produce the ethanol.

FIG. 1 shows a prior known process for producing ethanol from a lignocellulosic biomass starting material. The process is carried out in a sequential fashion. Each step must be completed before the next step can take place. In the first step 24, biomass solids 22 and aqueous sulfuric acid 20 are mixed and pretreated to facilitate subsequent hydrolysis of the biomass. The mixture proceeds to step two 26 where the hemicellulose is hydrolyzed. After the hemicellulose hydrolysis, the mixture is ready for step three 32 where base 31 is added to neutralize acid and adjust pH followed by addition of an enzyme 30 for the hydrolysis of cellulose to give simple sugars. The mixture of 32 after the hydrolysis reaction in complete will be a solution containing glucose and xylose from the biomass. This solution is then moved onto step four 38 where yeast 39 is added to ferment the sugars present in the solution to ethanol. After the fermentation is complete, the ethanol can be recovered 40 from the process solution by, for example, distillation.

One problem with this prior known process is that acids such as dilute sulfuric acid or other mineral acids are used, but these acids cause degradation of materials in the biomass to form substances that can act as inhibitors in subsequent enzymatic and fermentation steps. Material produced by sulfuric acid hydrolysis of the biomass would need to be purified before subsequent enzymatic and fermentation steps or larger amounts of enzyme or yeast would need to be used to overcome the inhibitors that would be present if no purification was done. Either way would increase the cost of carrying out the process.

SUMMARY

One embodiment of the present disclosure is a process for producing ethanol from lignocellulosic biomass comprising, treating lignocellulosic biomass with a dicarboxylic acid to hydrolyze hemicellulose of the lignocellulosic biomass to xylose, filtering the treated lignocellulosic biomass to obtain a solid material containing cellulose and a liquid portion containing xylose. The process also includes fermenting xylose of the liquid portion to provide a first ethanol containing material, hydrolyzing cellulose of the solid portion to provide a glucose containing medium, combining the first ethanol containing material with the glucose containing medium, fermenting the glucose containing medium after addition of the first ethanol containing material to provide a second ethanol containing material, isolating ethanol from the second ethanol containing material leaving a residue, and recovering the dicarboxylic acid from the residue to give a recovered dicarboxylic acid.

A further aspect of the above embodiment is treating additional lignocellulosic biomass with the recovered dicarboxylic acid.

Another embodiment of the present disclosure is a process for producing ethanol from lignocellulosic biomass comprising processing a first portion of lignocellulosic biomass. The processing comprises treating the lignocellulosic biomass with a dicarboxylic acid to hydrolyze hemicellulose of the lignocellulosic biomass to xylose, separating (e.g. filtering) the treated lignocellulosic biomass to separate a solid material containing cellulose from a liquid portion containing xylose, fermenting xylose in the liquid portion to provide a first ethanol containing material, hydrolyzing cellulose of the solid portion to provide a glucose containing medium, combining the first ethanol containing material with the glucose containing medium, fermenting the glucose containing medium to provide a second ethanol containing material, isolating ethanol from second ethanol containing material leaving a residue, and recovering the dicarboxylic acid from the residue. The process for producing ethanol from lignocellulosic biomass also includes treating a second portion of lignocellulosic biomass with the recovered dicarboxylic acid.

A further aspect of these embodiments is the dicarboxylic acid used in treating the lignocellulosic biomass to hydrolyze hemicellulose of the lignocellulosic biomass to xylose can be maleic acid or succinic acid.

Additional embodiments will be apparent from the descriptions herein.

DETAILED DESCRIPTION

Figure 1:
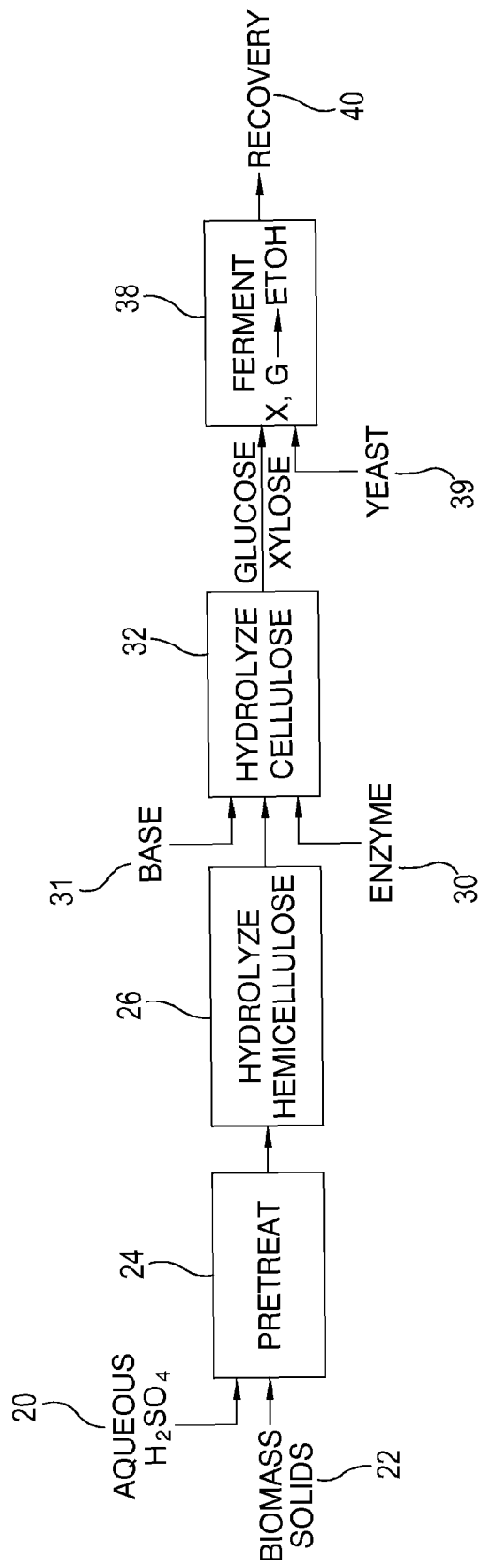
FIG. 1 is a block diagram of a prior art process to produce ethanol from lignocellulosic biomass that utilizes a sequential process.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As used herein, the term "glucan", is meant to mean a polysaccharide material containing glucose monomers such as cellulose. The terms "glucan" and "cellulose" can be used interchangeably within this disclosure.

As used herein, the term "lignocellulosic biomass", is meant to refer to any type of biomass comprising lignin and cellulose such as, but not limited to, non-woody plant biomass, agricultural wastes and forestry residues and sugar-processing residues. For example, the cellulosic feedstock can include, but is not limited to, grasses, such as switch grass, cord grass, rye grass, miscanthus, mixed prairie grasses, or a combination thereof; sugar-processing residues such as, but not limited to, sugar cane bagasse and sugar beet pulp; agricultural wastes such as, but not limited to, soybean stover, corn fiber from grain processing, corn stover, oat straw, rice straw, rice hulls, barley straw, corn cobs, wheat straw, canola straw, oat hulls, and corn fiber; and forestry wastes, such as, but not limited to, recycled wood pulp fiber, sawdust, hardwood, softwood, or any combination thereof. Further, the lignocellulosic biomass may comprise lignocellulosic waste or forestry waste materials such as, but not limited to, paper sludge, newsprint, cardboard and the like. Lignocellulosic biomass may comprise one species of fiber or, alternatively, a lignocellulosic biomass feedstock may comprise a mixture of fibers that originate from different lignocellulosic materials.

Typically, the lignocellulosic material will comprise cellulose in an amount greater than about 2%, 5% or 10% and preferably greater than about 20% (w/w) to produce a significant amount of glucose. The lignocellulosic material can be of higher cellulose content, for example at least about 30% (w/w), 35% (w/w), 40% (w/w) or more. Therefore, the lignocellulosic material may comprise from about 2% to about 90% (w/w), or from about 20% to about 80% (w/w) cellulose, or from 25% to about 70% (w/w) cellulose, or about 35% to about 70% (w/w) cellulose, or more, or any amount therebetween. The lignocellulosic material will also comprise hemicellulose in an amount greater than about 2%, 5% or 10%, and may comprise from 10% to about 50% (w/w), or from 15% to about 40% (w/w), or from 20% to about 35% (w/w), and can produce a significant amount of xylose.

Before lignocellulosic biomass can be treated with enzymes to breakdown the structure into constituent components, including fermentable sugars, the structure of the lignocellulosic biomass may be broken down. Breaking down the structure of the biomass allows enzymes that are used to hydrolyze the components, such as hemicellulose and cellulose, access to these components. Without treatment, lignocellulosic biomass is very resistant to enzyme attack utilized to breakdown the structure and provides simple sugars that can be converted into ethanol. This treatment can be done using acids to breakdown the structure. Acids such as dilute sulfuric acid or other mineral acids have been used, but these acids cause degradation of materials in the lignocellulosic biomass to form substances that can act as inhibitors in subsequent enzymatic and fermentation steps. Other acids that may be used include carboxylic acids and more particularly, dicarboxylic acids. It has been shown that a dicarboxylic acid may be used to treat lignocellulosic biomass to hydrolyze the hemicellulose and cellulose. The dicarboxylic acid acts like an enzyme mimic or a catalyst in the hydrolysis of the hemicellulose material or cellulose material that is found in lignocellulosic biomass, thus avoiding the cost of using an expensive enzyme to hydrolyze these materials. Using controlled conditions for the treatment of the lignocellulosic biomass with the dicarboxylic acids, the hydrolysis reaction can selectively hydrolyze mainly the hemicellulose component providing a liquid portion containing xylose, and leaving a solid portion in which the cellulose (glucan) component remains intact.

A variety of dicarboxylic acids may be used to treat the lignocellulosic biomass, preferable ones include maleic acid (as maleic acid or maleic anhydride) or succinic acid (as succinic acid or succinic anhydride). Amounts of acids that can be used to treat the lignocellulosic biomass range from 0.2 mMoles per gram of biomass to 2 mMoles per gram of biomass, or from 1 mMole per gram of biomass to 1.5 mMole per gram of biomass. The concentration amount of lignocellulosic biomass to be treated can range from 40 gm/liter to 200 gm/liter or from 100 gm/liter to 150 gm/liter. For effective treatment, the lignocellulosic biomass can be treated with the dicarboxylic acid at a temperature of 100° C. to 200° C., or from 150° C. to 170° C. for a time from 2 minutes to 60 minutes, or from 10 minutes to 30 minutes. Treatment of lignocellulosic biomass at appropriate times and temperatures using 50 mMole maleic acid may be used to achieve above 90% hydrolysis of hemicellulose to xylose at 40 g/l of corn stover. If the corn stover concentration is increased to 150 g/l, but keeping the amount of maleic acid of 50 mMole, only 55% hydrolysis of the hemicellulose is realized. Increasing of the dicarboxylic acid concentration so that dicarboxylic acid concentration to corn stover ratio is kept almost constant, maintains hydrolysis levels at 90%.

At an approximately constant dicarboxylic acid concentration to lignocellulosic biomass solids ratio (approximately 50 mM maleic acid at 40 g/L biomass solids and 200 mM maleic acid at 150 g/L biomass solids), the conversions of between 80 and 90% of hemicellulose to xylose can be achieved. While the use of maleic acid has many benefits, it is relatively expensive, and consequently processing the lignocellulosic biomass with the potential to recycle the maleic acid decreases costs. In certain embodiments, at least about 70% of the maleic or other dicarboxylic acid used to treat an amount of lignocellulosic biomass will be recycled, more desirably at least about 80%.

An advantage of using the catalytic properties of the maleic acid or other dicarboxylic acids relative to sulfuric acid or some other pretreatment methods results in minimal formation of degradation products formed during the hydrolysis of the hemicellulose or cellulose. Sulfuric acid causes significant formation of sugar degradation products, and some of these degradation products are enzyme and yeast inhibitors, resulting in the need to use larger amounts of enzymes and yeast to process the material. This lower amount of degradation product from hydrolysis with a dicarboxylic acid allows for smaller amounts of enzyme or yeast to be utilized than if a sulfuric acid hydrolysis or some other pretreatment methods were used. Lower amounts of degradation products also allows for the ready enzymatic hydrolysis of the glucan material to glucose, and the ready fermentation of the xylose to ethanol using a yeast without the necessity of purifying the material resulting from the dicarboxylic acid hydrolysis treatment.

Utilizing dicarboxylic acids to treat lignocellulosic biomass can result in the selective hydrolysis of the hemicellulose portion of the biomass with the result of obtaining a liquid portion of material rich in xylose from the hydrolyzed part and a solid portion rich in glucan material (glucose containing material or cellulose), which can be separated and further processed separately. Due to the initial processing with the dicarboxylic acid and formation and separation of the xylose-rich material, the solid portion rich in glucan material can contain a higher percentage (w/w) of cellulose than the starting lignocellulosic material, for example in certain embodiments having a w/w percentage of cellulose that is at least about 3% greater than the w/w percentage of cellulose in the starting lignocellulosic material. The xylose rich and glucan rich portions may be processed in parallel steps providing better throughput and a more efficient use of bioprocessing materials. Using the dicarboxylic acid to hydrolyze the hemicellulose to xylose provides a readily fermentable material due to minimal formation of degradation products that can acts as inhibitors, unlike using ordinary acids such as sulfuric acid. The xylose portion without further purifying can be fermented to ethanol using, for example, recombinant xylose-fermenting yeast, but other yeast may be utilized for the fermentation process.

If a solid cellulose material is desired as a product instead of ethanol, the glucan rich (glucose containing) solids portion can be isolated and further processed through steps such as dewatering and/or drying to obtain a cellulose material. Solid, dried cellulose can thus be obtained from lignocellulosic biomass. These results further indicate the benefit of the use of a dicarboxylic acid or more specifically, maleic acid in a novel process that generates glucan enriched solids.

As an alternative, the recovered glucan rich solids, which can have a higher percentage of cellulose than the starting lignocellulosic biomass material and thus provide a more concentrated input for hydrolysis of cellulose to glucose, can be further hydrolyzed using either a cellulase enzyme or other catalysts to break down the cellulose into fermentable sugar. For example, enzymatic hydrolysis of the remaining cellulose to glucose is essentially complete in 48 hours. In this regard, a cellulase enzyme is an enzyme that catalyzes the hydrolysis of cellulose to products such as glucose, cellobiose, and/or other cellooligosaccharides. Cellulase enzymes may be provided as a multienzyme mixture comprising exo-cellobiohydrolases (CBH), endoglucanases (EG) and beta-glucosidases (betaG) that can be produced by a number of plants and microorganisms. The process of the present invention can be carried out with any type of cellulase enzymes, regardless of their source; however, microbial cellulases provide preferred embodiments. Cellulase enzymes can, for example, be obtained from fungi of the genera *Aspergillus, Humicola*, and *Trichoderma*, and from the bacteria of the genera *Bacillus* and *Thermobifida*.

In certain aspects of this disclosure, the xylose rich portion can be fermented to give a first ethanol material also containing a yeast that was used in the xylose fermentation process. The first ethanol material can be added to the cellulose solids (glucan-rich) portion before, during or after the hydrolysis of the glucan material to form glucose. The combination of the first ethanol material with the glucan rich material or hydrosylate of such material, supplies yeast that can ferment the glucose formed from the hydrolysis step as it is occurring. The fermentation of the glucose in the combined material may be fermented without the addition of any further yeast, by utilizing the yeast supplied from the first ethanol material. However, additional yeast may be added during the fermentation step of the combined first ethanol material and the glucan rich material or hydrosylate. This consolidated bioprocessing decreases yeast cost and decreases processing time by allowing the fermentation and hydrolysis to occur in the same processing step.

The fermentation of the sugars to produce ethanol can be conducted with any of a wide variety of fermentive microorganisms such as yeast or bacteria, or other genetically modified versions of yeasts, including recombinant xylose-fermenting yeast, and using known techniques.

The ethanol can then be purified from the fermented medium, for example by distillation. An ethanol yield of approximately 90% of theoretical was shown by utilizing maleic acid hydrolysis of the lignocellulosic biomass. The ability to obtain a high yield of ethanol from lignocellulosic biomass using maleic acid hydrolysis without having to further treat or purify the resulting material from the hydrolysis before fermentation indicates the absence of inhibitors that would otherwise decrease rate and yield of the ethanol fermentation.

Economic use of a dicarboxylic acid catalyst is achieved by the recovery and reuse of the dicarboxylic acid in a processing sequence enabling its benefits to be realized. In one aspect of the process, in order to avoid the formation of ionic forms of the dicarboxylic acid, a neutralization agent such as ammonia, aqueous ammonia (ammonium hydroxide), or any other basic nitrogen compound able of neutralizing an acidic compound could be used. However, in another aspect of the process other neutralization agents may be used such as alkali or alkaline hydroxide or oxides, or any other basic neutralization agent known in the art. After the ethanol has been recovered from the neutralized fermentation material by, for example distillation, the material remaining is rich in the dicarboxylic acid. The dicarboxylic acid can then be recovered from this material, for example, by through distillation. Once the recovery step is complete, the dicarboxylic acid would be recycled to the front of the process to treat additional amounts of lignocellulosic biomass. The extent of recycle would be a function of cost of recovery as well as stability of the acid during a distillation step. The distillation itself could be carried out under a vacuum in order to minimize formation of salts in the bottoms from the distillation column and also preserve the activity of the dicarboxylic acid. For example, maleic acid has a high boiling point and is stable up to 220° C., and may be recovered and concentrated in the bottoms stream of the fermentation distillation column itself. Further evaporation would then give a concentrated maleic acid stream which would then be recycled to the front end of the process for further treatment of additional lignocellulosic biomass. Other methods of dicarboxylic acid recovery may be through adsorption, acidification, chromatography, crystallization or precipitation or a combination of these methods. These process steps that allow the dicarboxylic acid to be recycled can be used to reduce catalyst costs of the total process.

Figure 2:
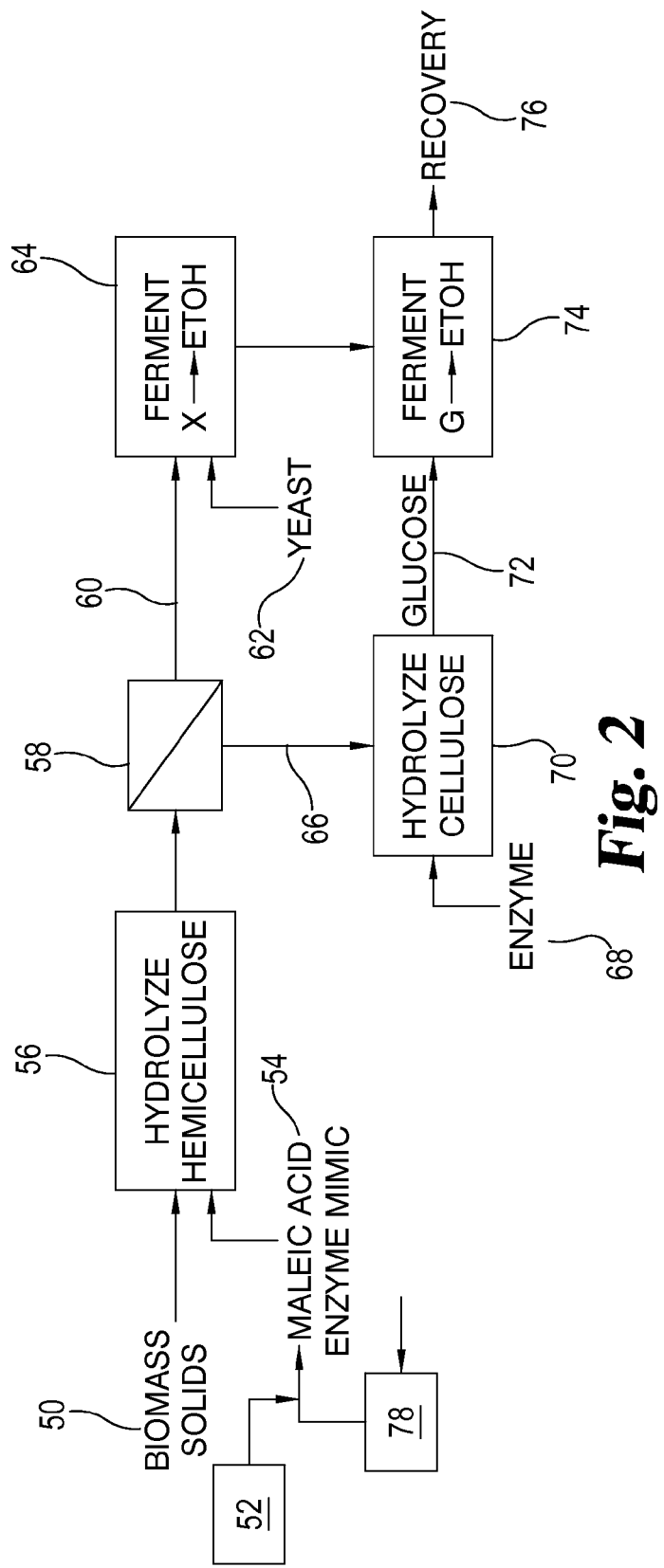
FIG. 2 is a block diagram of the presently disclosed process for the production of ethanol from lignocellulosic biomass using a dicarboxylic acid as an enzyme mimic that allow the parallel processing of streams and recycling of the dicarboxylic acid.

With reference now to FIG. 2, one embodiment of treating lignocellulosic biomass with a dicarboxylic acid including recycling of the dicarboxylic acid to the front of the process is shown. In this figure, the dicarboxylic acid used is maleic acid. Lignocellulosic biomass 50 and maleic acid 54 are mixed and reacted to hydrolyze 56 the hemicellulose portion of the biomass 50 to provide a liquid portion containing xylose. The maleic acid 54 may be made up of recycled maleic acid 78 reclaimed during recovery of ethanol and fresh additional maleic acid 52, which may be added as either maleic acid or as maleic anhydride. Fresh maleic acid 52 may make up the bulk of maleic acid 54 added to the hemicellulose hydrolysis 56 especially when starting the process anew when there is little to no recycled maleic acid 78 available.

After the hydrolysis of the hemicellulose 56 is complete, the resulting mixture of xylose solution and solids containing cellulose (glucan) are sent to a separation device 58 to separate the solids and liquids. For example, a filter could be used, but any other device used in the art for solid/liquid separations may be used. The liquid portion 60 containing xylose is sent to a fermentation step 64 where yeast 62 is added and the xylose is fermented to ethanol to produce a first ethanol containing material. The yeast 62 may be a yeast able to ferment both xylose and glucose, or may be a recombinant xylose fermenting yeast, or other organisms or yeast known in the art to ferment sugars to ethanol.

The solids 66 from the separation, which contain cellulose (glucose containing material or glucan), may be sent to a hydrolysis step 70 where an enzyme 68 is added to the solids 66 and the mixture is subjected to normal enzymatic hydrolysis conditions which may include pH adjustments and temperature controls to provide a glucose containing material. The hydrolysis step 70 may occur at nearly the same time as the fermentation step 64 of the xylose. After both the xylose fermentation step 64 and the cellulose hydrolysis step 70 are complete, the resulting material of both these steps is combined in a glucose fermentation step 74. Combining the first ethanol containing material from the fermentation of the xylose with the glucose containing material allows for the fermentation of the glucose 72 from the cellulose hydrolysis 70 without needing to add more yeast. The yeast grown during the xylose fermentation 64 can be used for the glucose fermentation 74 thus adding to the efficiency of the process.

After the fermentation of the glucose is complete, a second ethanol material is obtained which is sent for recovery 76 of the ethanol. Recovery of the ethanol may be done through distillation. The residue after ethanol recovery will be rich in maleic acid and is further treated by either additional reduce pressure distillation, or a crystallization step to recover the maleic acid, however it should be understood that other methods known in the art for the recovery of a carboxylic acid could be used to recover the maleic acid. The recovered maleic acid can then be recycled 78 back to the front of the process 54, where fresh maleic acid 52 may be added to be used in the treatment of additional portions of lignocellulosic biomass.

Example 1

Corn stover or other lignocellulosic materials (biomass) enters the process where it is mixed with maleic acid (in water) as an enzyme mimic. Cooking of the mixture of maleic acid and biomass material at between 150° C. and 170° C. for periods of 2 minutes to 30 minutes is carried out. The hydrolysis of 40 g/l of corn stover uses a maleic acid concentration of 50 mM, while 150 g/l of corn stover uses the proportionally higher concentration of 200 mM maleic acid, thereby keeping the diacid:corn stover ratio at a nearly constant level. The xylose-rich liquid and glucan-rich solid portions of the hydrolyzed mixture are separated by filtration. The addition of cellulase enzyme to the glucan-rich portion results in 90% hydrolysis of cellulose to glucose at concentrations of lignocelluloses of up to 150 g/l producing a sugar solution that is readily fermented.

The fermentation of the xylose-rich liquid was carried out at a pH of approximately 6, with the maleic acid being neutralized using calcium hydroxide, and then fermenting the resulting xylose-rich material at 30° C. for 72 hours. Once the fermentation is completed, the ethanol is recovered through distillation, and consequently the maleic acid (which has a high boiling point and is stable up to 220° C.) is recovered and may be concentrated in the bottoms stream of the fermentation column. Further evaporation would then give a concentrated maleic acid stream which would be then recycled to the front end of the process for use in further treatment of additional biomass. Recovery of 80% of the maleic acid would result in enzyme or enzyme mimetic costs of less than 20¢/gal when combined with consolidated bioprocessing. This is a potentially attractive process for the manufacture of ethanol when enzyme costs can exceed several dollars/gallon according to the literature.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A process for producing ethanol from lignocellulosic biomass comprising:
   treating a lignocellulosic biomass with a dicarboxylic acid to hydrolyze hemicellulose of the lignocellulosic biomass to xylose;
   separating the treated lignocellulosic biomass to obtain a solid portion containing cellulose and a liquid portion containing xylose;
   fermenting the liquid portion containing xylose to provide a first ethanol containing material;
   hydrolyzing cellulose of the solid portion to provide a glucose containing medium;
   combining the first ethanol containing material with the glucose containing medium;
   fermenting the glucose containing medium after addition of the first ethanol containing material to provide a second ethanol containing material;
   isolating ethanol from the second ethanol containing material leaving a residue; and
   recovering the dicarboxylic acid from the residue to give a recovered dicarboxylic acid.

2. The process of claim 1 further comprising treating additional lignocellulosic biomass with the recovered dicarboxylic acid to hydrolyze hemicellulose of the lignocellulosic biomass to xylose.

3. The process of claim 1 wherein the combining of the first ethanol containing material with the glucose containing medium occurs before the hydrolyzing of the cellulose of the solid portion is complete.

4. The process of claim 1 wherein a yeast used in fermenting the glucose containing medium is supplied only from the first ethanol containing material.

5. The process of claim 1 wherein the dicarboxylic acid is maleic acid.

6. The process of claim 1 wherein the dicarboxylic acid is succinic acid.

7. The process of claim 1 wherein the liquid portion containing xylose is neutralized with a neutralization agent before the step of fermenting the liquid portion containing xylose.

8. The process of claim 7 wherein the neutralization agent is a basic nitrogen compound.

9. The process of claim 1, wherein:
said fermenting the liquid portion containing xylose step is conducted with a yeast able to ferment both xylose and glucose to ethanol so that said yeast is contained in the first ethanol containing material; and
said fermenting the glucose containing medium step is conducted with said yeast contained in the first ethanol containing material.

10. The process of claim 9, wherein:
said combining the first ethanol containing material with the glucose containing medium step includes combining the first ethanol containing material with a glucan material containing cellulose of said solid portion before or during said hydrolyzing cellulose step; and
said yeast ferments glucose to ethanol during said hydrolyzing cellulose step.

11. The process of claim 1, wherein said solid portion of said separating step and said hydrolyzing step comprises a lignocellulose solid portion.

12. A process for producing ethanol from lignocellulosic biomass comprising:
processing a first portion of lignocellulosic biomass, the processing comprising:
treating the lignocellulosic biomass with a dicarboxylic acid to hydrolyze hemicellulose of the lignocellulosic biomass to xylose;
separating the treated lignocellulosic biomass to separate a solid portion containing cellulose from a liquid portion containing xylose;
fermenting the liquid portion containing xylose to provide a first ethanol containing material;
hydrolyzing cellulose of the solid portion to provide a glucose containing medium;
combining the first ethanol containing material with the glucose containing medium;
fermenting the glucose containing medium to provide a second ethanol containing material;
isolating ethanol from second ethanol containing material leaving a residue; and
recovering the dicarboxylic acid from the residue; and
treating a second portion of lignocellulosic biomass with the recovered dicarboxylic acid.

13. The process of claim 12 wherein the combining of the first ethanol containing material with the glucose containing medium occurs before the hydrolyzing of the cellulose of the solid portion is complete.

14. The process of claim 12 wherein a yeast used in fermenting the glucose containing medium is supplied only from the first ethanol solution.

15. The process of claim 12 wherein the dicarboxylic acid is maleic acid.

16. The process of claim 12 wherein the dicarboxylic acid is succinic acid.

17. The process of claim 2 wherein the liquid portion containing xylose is neutralized with a neutralization agent before the step of fermenting the liquid portion containing xylose.

18. The process of claim 17 wherein the neutralization agent is a basic nitrogen compound.

19. The process of claim 12, wherein:
said fermenting the liquid portion containing xylose step is conducted with a yeast able to ferment both xylose and glucose to ethanol so that said yeast is contained in the first ethanol containing material; and
said fermenting the glucose containing medium step is conducted with said yeast contained in the first ethanol containing material.

20. The process of claim 19, wherein:
said combining the first ethanol containing material with the glucose containing medium step includes combining the first ethanol containing material with a glucan material containing cellulose of said solid portion before or during said hydrolyzing cellulose step; and
said yeast ferments glucose to ethanol during said hydrolyzing cellulose step.

* * * * *